(12) United States Patent
Woelfle-Gupta et al.

(10) Patent No.: US 12,201,647 B2
(45) Date of Patent: Jan. 21, 2025

(54) INDUCING CASPASE ACTIVITY

(71) Applicant: Dow Global Technologies LLC, Midland, MI (US)

(72) Inventors: Caroline Woelfle-Gupta, Midland, MI (US); Andrew Scott, Midland, MI (US); Matthew LeBaron, Midland, MI (US); Daniel Wilson, Midland, MI (US); Susan L. Jordan, Doylestown, PA (US); Robert L. Schmitt, Harleysville, PA (US); Raja Settivari, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 732 days.

(21) Appl. No.: 17/435,110

(22) PCT Filed: Feb. 26, 2020

(86) PCT No.: PCT/US2020/019804
§ 371 (c)(1),
(2) Date: Aug. 31, 2021

(87) PCT Pub. No.: WO2020/180549
PCT Pub. Date: Sep. 10, 2020

(65) Prior Publication Data
US 2022/0125830 A1    Apr. 28, 2022

Related U.S. Application Data

(60) Provisional application No. 62/813,819, filed on Mar. 5, 2019.

(51) Int. Cl.
*A61K 31/765* (2006.01)
(52) U.S. Cl.
CPC ................... *A61K 31/765* (2013.01)
(58) Field of Classification Search
CPC ..................... A61K 31/765; A61K 31/77
See application file for complete search history.

(56) References Cited

U.S. PATENT DOCUMENTS

| | | | |
|---|---|---|---|
| 6,939,563 B2 | 9/2005 | Corpet et al. | |
| 2004/0028804 A1 | 2/2004 | Anderson et al. | |
| 2009/0074704 A1* | 3/2009 | Zhao | C08G 65/3314 424/78.17 |
| 2009/0252702 A1 | 10/2009 | Bruce et al. | |
| 2010/0303878 A1 | 12/2010 | Slager et al. | |
| 2015/0359751 A1* | 12/2015 | Lee | A61K 49/221 424/490 |
| 2016/0228467 A1 | 8/2016 | Stein et al. | |

FOREIGN PATENT DOCUMENTS

WO    0071564 A2    11/2000

OTHER PUBLICATIONS

International Preliminary Report on Patentability for related PCT Application PCT/US2020/019804, mailed Sep. 16, 2021 (8 pgs).
International Search Report & Written Opinion for related PCT Application PCT/US2020/019804, mailed Jun. 18, 2020 (12 pgs).
Howley, et al., "Caspases as Therapeutic Targets"; Journal of Cellular and Molecular Medicine, vol. 12, No. 5A, Sep. 1, 2008 (14 pgs).
Herzberger, et al., "Polymerization of Ethylene Oxide, Propylene Oxide, and Other Alkylene Oxides: Synthesis, Novel Polymer Architectures and Bioconjugation"; Chemical Reviews, vol. 116, No. 4, Feb. 24, 2016 (74 pgs).
Eskandani, et al., "Cyto/Genotoxicity Study of Polyoxyethylene (20) Sorbitan Monolaurate (Tween 20)"; DNA and Cell Biology, vol. 32, No. 9, Sep. 1, 2013 (6 pgs).
Eskandani, Morteza et al., "Cyto/Genotoxicity Study of Polyoxyethylene (2) Sorbitan Monolaurate (Tween 20)", DNA and Cell Biology, vol. 32, No. 9, pp. 498-503, Jun. 10, 2013.
Cui, Min et al., "A highly sensitive biosensor for tumor maker alpha fetoprotein based on poly(ethylene Glycol) doped conducting polymer PEDOT", Biosensors and Bioelectronics, vol. 29, pp. 763-741, Jan. 6, 2016.

* cited by examiner

*Primary Examiner* — Andrew S Rosenthal
(74) *Attorney, Agent, or Firm* — Arthur R. Rogers

(57) ABSTRACT

Embodiments are directed towards methods of inducing caspase activity. The methods include contacting a cell with a treatment compound formed by alkoxylation of an initiator using an oxide.

13 Claims, No Drawings

INDUCING CASPASE ACTIVITY

This application is a National Stage Application under 35 U.S.C. § 371 of International Application Number PCT/US2020/019804, filed Feb. 26, 2020 and published as WO 2020/180549 on Sep. 10, 2020, which claims the benefit to U.S. Provisional Application 62/813,819, filed Mar. 5, 2019, the entire contents of which are incorporated herein by reference in its entirety

FIELD OF DISCLOSURE

Embodiments of the present disclosure are directed towards methods inducing caspase activity.

BACKGROUND

Cancer is a group of diseases involving abnormal cell growth. Colorectal cancer, which may be referred to as colon cancer or bowel cancer, is a cancer from uncontrolled cell growth in the colon or rectum.

Colorectal cancer is a commonly diagnosed malignancy. Treatments for colorectal cancer can include surgery, radiation therapy, and/or chemotherapy. However, there remains a need for new methods and/or new compositions that may be utilized for treatment.

SUMMARY

The present disclosure provides methods of inducing caspase activity, the method comprising contacting a cell with a treatment compound formed by alkoxylation of an initiator using an oxide.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION

While not wishing to be bound to theory, one mechanism involved in the development of colorectal cancer is the mutation of the APC (Adenomatous Polyposis *Coli*) gene, which produces the APC protein. The APC protein is part of a protein-based destruction complex that helps to prevent the accumulation of the β-catenin protein in a cell. The APC protein and the β-catenin protein are part of one of the WNT (Wingless/Integrated) signaling transduction pathways that pass signals into a cell through cell surface receptors. In general, when cells are stimulated by WNT, the destruction complex is deactivated, and β-catenin protein will enter the nucleus and bind to the transcription factor (TCF) which controls the transcription of genetic information. The genes involved in regular cell progression will be activated and it is a regulated process. Without the APC protein, β-catenin protein will continuously accumulate to high levels and translocate into the nucleus, bind to the TCF, which can then bind to DNA, and activate the transcription of proto-oncogenes. When proto-oncogenes are inappropriately expressed at high levels, they become oncogenes. Activated oncogenes can cause cells designated for apoptosis to survive and proliferate instead, which can lead to the development of colorectal cancer, in an individual.

Methods of inducing caspase activity are disclosed herein. Advantageously, inducing caspase activity can incite apoptosis, i.e. induce cell death. For a number of applications, apoptosis is desirable, as compared to necrosis. Inducing caspase activity can provide for degradation of a number of intracellular proteins to result in cell death. Cell death by apoptosis can be a desirable effect on colorectal cancer cells, for instance.

As used herein, "a", "an", "the", "at least one", "a number of", and "one or more" may be used interchangeably unless indicated otherwise. The term "and/or" means one, one or more, or all of the listed items. The recitations of numerical ranges by endpoints include all numbers subsumed within that range, e.g., 1 to 5 includes 1, 1.5, 2, 2.75, 3, 3.80, 4, 5, etc.

The methods of inducing caspase activity, as disclosed herein, include contacting a cell with a treatment compound. As used herein, "treatment compound" refers to compounds that may formed by alkoxylation of an initiator using an oxide.

Embodiments of the present disclosure provide that the initiator includes compounds containing three or more reactive available hydroxyl groups, amine groups, or combinations thereof. One or more embodiments provide that the initiator can be selected from glycerol, diglycerol, triglycerol, hexaglycerol, tripentaerythritol, trimethylolpropane, sorbitol, ethylenediamine, triethyleneamine, 2,2 bis(hydroxymethyl)-1,3-propanediol, ethanolamine, and combinations thereof.

Embodiments of the present disclosure provide that the oxide can be selected from ethylene oxide, propylene oxide, butylene oxide, and combinations thereof.

One or more embodiments of the present disclosure provide that the treatment compound formed by alkoxylation of an initiator using an oxide may be represented by the following Formula I:

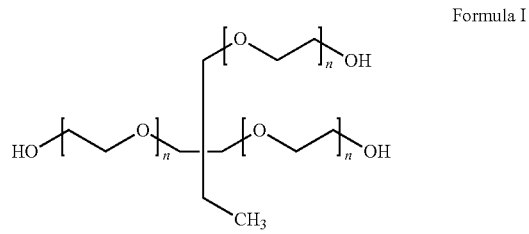

Formula I where each n is independently from 1 to 303.

An example of the treatment compound represented by Formula I is trimethylolpropane ethoxylate.

One or more embodiments of the present disclosure provide that the treatment compound may be represented by the following Formula II:

Formula II

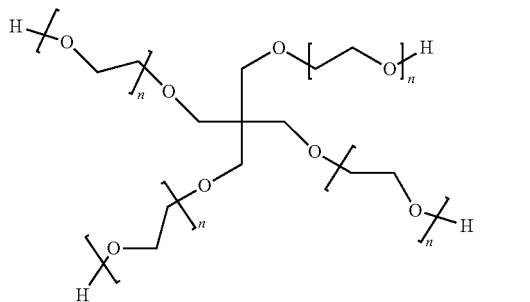

where each n is independently from 1 to 227.

An example of the treatment compound represented by Formula II is 4-arm poly(ethylene glycol).

One or more embodiments of the present disclosure provide that the treatment compound may be represented by the following Formula III:

Formula III

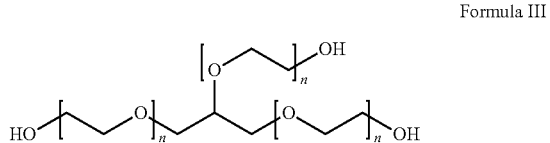

where each n is independently from 1 to 303.

An example of the treatment compound represented by Formula III is glycerol ethoxylate.

Embodiments of the present disclosure provide that the treatment compound has a number average molecular weight (Mn) from 400 to 40,000 g/mol. All individual values and subranges from 400 to 40,000 g/mol are included; for example, the treatment compound can have Mn from a lower limit of 400, 450, 500, 600, 700, 800, 900, or 1000 g/mol to an upper limit of 40,000, 30,000, 20,000, 15,000, or 10,000 g/mol.

The treatment compound may be prepared, e.g., alkoxylation of the initiator using the oxide, using known methods, equipment, and/or conditions, which may vary for different applications. The treatment compound may be obtained commercially.

As mentioned, methods of inducing caspase activity, as disclosed herein, include contacting a cell with the treatment compound. One or more embodiments of the present disclosure provide that contacting the cell with the treatment compound occurs in vivo. One or more embodiments of the present disclosure provide that contacting the cell with the treatment compound occurs in vitro. The cell may be contacted with the treatment compound by utilizing a number of different known methods, equipment, and/or conditions. Various methods, equipment, and/or conditions may be utilized for different applications The treatment compound may be utilized with a known treatment medium. For instance, the treatment compound may be dissolved, to provide an effective amount, in a known treatment medium prior to contacting the cell. One or more embodiments provide that the treatment compound and the treatment medium may be combined to form a solution. The solution may be a homogeneous solution. Examples of treatment mediums include, but are not limited to, DMEM (Dulbecco's Modified Eagle Medium), RPMI 1640, and McCoy's 5A, and combinations thereof, among others. A number of treatment mediums are commercially available.

The treatment compound can have a 0.001 millimolar (mM) to 75 mM concentration in the treatment medium. All individual values and subranges from 0.001 to 75 mM are included; for example, the effective concentration can be from a lower limit of 0.001, 0.005, 0.01, 0.1 or 1.0 mM to an upper limit of 75, 72, 70, 68, or 65 mM of the treatment compound in the treatment medium.

The cell may be contacted with an effective amount of the treatment compound. As used herein, the term "effective amount", which may be used interchangeably with "therapeutic effective amount" and/or "therapeutic amount", refers to an amount of the treatment compound that is sufficient to provide the intended application, e.g., induce caspase activity. Contacting the cell with an effective amount of the treatment compound may desirably provide a disease treatment, e.g., a colorectal cancer treatment, where undesirable cells are subject to cell death by apoptosis that results from inducing caspase activity. The effective amount may vary depending upon the particular application, e.g., in vitro or in vivo, the subject being treated, e.g., the weight and age of the subject, the severity of the disease condition, and/or the manner of administration, among other considerations, which can readily be determined by one of ordinary skill in the art. As used herein, a "subject" that is treated refers to any member of the animal kingdom, e.g., mammals, including humans.

Embodiments of the present disclosure provide that specific doses may vary depending on the particular treatment compound utilized, the dosing regimen to be followed, timing of administration, and/or the physical delivery system in which the treatment compound is carried. For instance, the effective amount of the treatment compound may be contacted with the cell by a single dosing or by multiple dosings.

Embodiments of the present disclosure provide that the cell that is contacted with the treatment compound is a cancerous cell. For instance, the cell may be a colorectal cancer cell. Colorectal cancer cells may also be referred to as colon cancer cells, bowel cancer cells, and/or colorectal adenocarcinoma cells. One or more embodiments of the present disclosure provide that additional cells, i.e. non-cancerous cells, may be contacted with the treatment compound.

While not intending to be bound by theory, caspases, which may be referred to as cysteine-aspartic acid proteases, are a family of cysteine proteases involved in apoptosis. There are two types of caspases: initiator caspases, which include caspase 2,8,9,10,11,12, and effector caspases, which include caspase 3,6,7. One or more embodiments of the present disclosure provide that contacting a cell with a treatment compound induces an effector caspase activity. One or more embodiments of the present disclosure provide that the caspase is selected from caspase 3, caspase 6, caspase 7, or combinations thereof.

As mentioned, inducing caspase activity can advantageously incite apoptosis. Induced caspase activity may be determined by a number of different known methods, equipment, and/or conditions. For instance, induced caspase activity may be evidenced by an average relative caspase activity greater than one (>1), e.g., for a number of experimental runs, as determined by Caspase-Glo 3/7 Assay 4.B. Standard Protocol for Cells in a 96-Well Plate, available from Promega. As used herein, "relative caspase activity" can be utilized interchangeably with relative apoptosis.

Utilizing the treatment compound, as discussed herein, may advantageously provide an improved, i.e. reduced, laxative effect, as compared to some other polymeric compounds utilized for cancer treatment. This reduced laxative effect may help to provide a desirable increase with patient compliance, as compared to some other polymeric compounds associated with a relatively greater laxative effect.

One or more embodiments of the present disclosure provide a method of treating colorectal cancer. The method can include contacting a colorectal cancer cell with the treatment compound.

One or more embodiments of the present disclosure provide a method of treating cancer. The method can include administering the treatment compound to a mammal.

Examples

In the Examples, various terms and designations for materials are used including, for instance, the following:
Trimethylpropane ethoxylate (Mn of 1014 g/mol; obtained from Sigma-Aldrich);
4-arm poly(ethylene glycol) (Mn of 10,000 g/mol; obtained from Sigma-Aldrich);
Glycerol ethoxylate (Mn of 1000 g/mol; obtained from Sigma-Aldrich);
Cells (human colon; colorectal adenocarcinoma; HT-29 (ATCC® HTB-3); obtained from ATCC);
McCoy's 5A (growth medium; obtained from ThermoFisher Scientific);
Fetal bovine serum (obtained from ATCC);
Dulbecco's Phosphate-Buffered Saline (GIBCO 14190-144; obtained from ThermoFisher Scientific);
Complete Growth Medium (ATCC® 30-2007; obtained from ATCC);
Trypsin-EDTA (GIBCO Trypsin-EDTA (0.25%); Catalog number 25200056; obtained from ThermoFisher Scientific);
Thiazolyl Blue Tetrazolium Bromide (obtained from ThermoFisher Scientific);
Dulbecco's Phosphate-Buffered Saline with calcium and magnesium (GIBCO 14040-133; obtained from ThermoFisher Scientific);
Caspase-Glo 3/7 Assay (luminescent assay; Catalog number G8093; obtained from Promega);
Dimethyl sulfoxide (Catalog number 276855; obtained from Sigma-Aldrich).

Culture Initiation and Maintenance

Culture initiation and maintenance was performed as follows. Culture initiation and maintenance was performed in accordance with "Thawing, Propagating, and Cryopreserving Protocol" NCI-PBCF-HTB38 (HT-29) Colon Adenocarcinoma (ATCC®HTB-38™); Feb. 27, 2012; Version 1.6.

HT-29 (ATCC® HTB-38™) cells (which contained approximately $1 \times 10^6$ cells per mL) were initiated and seeded into a T-25 flask containing McCoy's 5A and fetal bovine serum (10% (v/v)). Then, ATCC® 30-2007 (warmed in 37° C. water bath for at least 15 minutes) was used to expand the HT-29 cells. The cells were grown in a humidified incubator (SANYO INCT-16-CMT; MCO-19AIC (UV)) maintained at 37° C. and 5% $CO_2$. Then, the cells were rinsed with 1× Dulbecco's Phosphate-Buffered Saline and sub-cultured in T-75 flasks 1 to 3 times per week using 1× Trypsin-EDTA, applied for ≤5 minutes; enzymatic action of the trypsin-EDTA was stopped by adding complete growth medium to the detached cells. Then, upon reaching 80 to 90% confluency the cells were split into the following split ratio ranges: 1:5 to 1:16. Subculture and growth expansion activities were recorded, such as passage number, % confluency, % viability (only on experimental set-up day), and cell morphology throughout all phases. The cells were maintained in log-phase growth.

Cell Culture Plating (Day 0)

Cell culture plating was performed as follows. A cell suspension from a single 80 to 90% confluent T-75 flask was harvested with trypsin-EDTA and complete growth medium. To obtain cell concentration and viability, cell counts were obtained using a COUNTESS automated cell counter (INVITROGEN C10227; CNTR-7-CMT) in which 2 chambers of each slide were provided with 10 µL each of 1:1, 0.4% trypan-blue dye (INVITROGEN T10282) and cell suspension. Cell counts and percent viability were averaged from both chambers of a single slide. Then, viable cells (defined as viability≥90%) containing complete growth medium were plated onto sterile 96-well plates using a multi-channel pipette. Per cell density, between 5000 and 6000 cells per well (40,000 to 48,000 cells per mL) were added to each well, except for wells that were utilized as 'saline only' no cell control wells; equal volumes each of 125 µL of cell suspension were added per well beginning with row A to H on the plate. The plates used for each of 2 endpoints, apoptosis and cytotoxicity, were solid white plates and clear plates, respectively. The cells were incubated for 24±2 hours to allow attachment.

Trimethylpropane Ethoxylate/4-Arm Poly(Ethylene Glycol)/Glycerol Ethoxylate Stock Preparation Stock solutions were prepared at respective target concentrations of trimethylpropane ethoxylate, 4-arm poly(ethylene glycol), and glycerol ethoxylate in sterile saline. For the assays, based on the solubility limits due to high molecular weight, adjustments to lower stock concentration preparations (w/v) to generate either a solution or a pipettable suspension were made if necessary, or solubilization was achieved by adding small increments of saline, continuous mixing, vortexing, sonicating, or stirring prior to use in assay. If necessary for solubilization, the saline was pre-heated to 37° C. prior to mixing with the trimethylpropane ethoxylate, 4-arm poly(ethylene glycol), and/or glycerol ethoxylate. Total volumes of 10 mL were prepared per tested substance on the day of cell suspension plating (Day 0).

Cytotoxicity Reagent Preparation

Thiazolyl blue tetrazolium bromide was prepared at 5 mg/mL in Dulbecco's Phosphate-Buffered Saline with calcium and magnesium. Total volumes of 30 mL were prepared (w/v) per set-up day (Day 0) and stored at 4° C. until use.

Dosing Solution Preparation (Day 0)

Dosing solutions/suspensions of each test substance stock were prepared in a total of 15 mL each of McCoy's 5A and 1% fetal bovine serum. Various amounts of dosing stock were utilized to achieve dosing solutions/suspensions from 0.0015 to 60 mM. The dosing solutions/suspensions were prepared in sterile reservoirs and repeatedly mixed with a pipette until visible uniformity was achieved. Using a 2 mL capacity sterile 96-deep well block, 2 mL of dosing solution/suspension was added to each of 6 replicate wells for the treatment groups and each of 12 wells for the saline only cell controls and saline only 'no cell' background correction controls. The plates were established following a semi-randomized statistical design. Each test substance was identified numerically and via a color code used for identifying wells to be treated. The blocks were covered with sealing tape, plate lid and placed into a 4° C. lab refrigerator (Fischer Scientific, 135B1; RFR-22-CMT) overnight.

Treatment (Day 1)

All 96-deep well blocks containing dosing solutions/suspensions were removed from the refrigerator and placed in a 37° C. bead bath for a minimum of 30 minutes. Approximately 24 hours after plating, well plates were removed from the incubator and treated one at a time. All wells from a cell plate were aspirated using a 6-well aspirating device starting with row A to H. Using a multi-channel pipette, 100 µL each of dosing solution/suspension (from the blocks) was added to each well of the 96-well cell treatment plate; starting from row A to row H (same order). All wells were aspirated and treated 2 rows at a time to prevent well drying and maintain cell attachment and viability; pipette tips were changed per row. All plates were placed into the incubator and allowed to treat for 24±2 or 48±2 hours prior to harvest.

Harvest (Day 2 and Day 3)

Apoptosis

Assessment of apoptosis was performed as follows. Apoptosis was performed in accordance with "Caspase-Glo 3/7 Assay" 4.B. Standard Protocol for Cells in a 96-Well Plate (Promega). The Caspase-Glo 3/7 Assay components were pre-warmed to room temperature for approximately 60 minutes. White plates were removed (one at a time) from the incubator and the treatment medium was aspirated. Using a multi-channel pipette, 100 µL of 1× Dulbecco's Phosphate-Buffered Saline was added to each well of the 96-well plate. The Assay reagents (buffer and substrate) were manually mixed and added to a reagent reservoir; using a multi-channel pipette, 100 µL of the Assay reagent mixture was added to each well of the 96-well plate. The plate(s) (protected with foil from light) were placed on a plate shaker and allowed to rotate for 5 minutes at approximately 800 rpm at room temperature. The plates were then incubated at room temperature for an additional 25 minutes prior to analysis. Luminescence was recorded in terms of Relative Light Units (RLU) for each plate on a FLUOstar Omega Plate Reader.

Cytotoxicity

Assessment of cytotoxicity was performed as follows. Cytotoxicity reagent (5 mg/mL), as previously described, was pre-warmed to room temperature for approximately 30 minutes and then diluted into 1× Dulbecco's Phosphate-Buffered Saline with calcium and magnesium to provide a concentration of 0.675 mg/mL (final). Clear plates were removed from the incubator (one at a time) and the treatment medium was aspirated. Using a multi-channel pipette, 200 µL of the cytotoxicity reagent (final) was added to each well of the 96-well plate; then the plates were covered with sealing tape and incubated in a humidified 37° C. incubator for 4 hours. Following incubation, the supernatant was aspirated and dimethyl sulfoxide (200 µL) was added to each well. Following thorough mixing by repeat pipetting, the cell lysate was transferred to a new clear 96-well plate and absorbance was quantified at 600 and 630 nm on a FLUOstar Omega Plate Reader.

Analysis

Relative caspase activity was calculated as follows:

$(RLU_{Foreground}) - (RLU_{Saline\ Only\ 'no\ cell'\ control}) = (RLU_{Background\ corrected})$;

$((RLU_{Background\ corrected})$ of each test substance containing well)/(Average $(RLU_{Foreground})$ of 12 saline only control wells)=relative caspase activity; where RLU=relative light unit.

Relative caspase activity of each test substance containing well/6 replicates=Average relative caspase activity. The results are reported in Tables 1, 3, and 5 for the various utilized concentrations.

Cell viability was calculated as follows:

$(Abs_{600\ Foreground}) - (Abs_{600\ Saline\ Only\ 'no\ cell'\ control}) = (Abs_{600\ Background\ corrected})$ $(Abs_{630\ Foreground}) - (Abs_{630\ Saline\ Only\ 'no\ cell'\ control}) = (Abs_{630\ Background\ corrected})$ $(Abs_{600\ Background\ corrected}) - (Abs_{630\ Background\ corrected}) = (Abs_{600-630})$ $((Abs_{600-630})$ of each test substance containing well)/(Average $(Abs_{600-630})$ of 12 saline only control wells)=% Cell Viability % Cell Viability of each test substance containing well/6 replicates=Average % Cell Viability. The results are reported in Table 2, 4, and 6 for the various utilized concentrations.

TABLE 1

|  | Trimethyl-propane ethoxylate [15 mM] | Trimethyl-propane ethoxylate [30 mM] | Trimethyl-propane ethoxylate [60 mM] |
| --- | --- | --- | --- |
| Average relative caspase activity (Run 1) | 1.20 | 1.25 | 1.58 |
| Standard deviation relative caspase activity (Run 1) | 0.11 | 0.11 | 0.09 |
| Average relative caspase activity (Run 2) | 1.39 | 1.32 | 0.99 |
| Standard deviation relative caspase activity (Run 2) | 0.13 | 0.09 | 0.10 |
| Average relative caspase activity (Run 3) | 1.19 | 1.35 | 1.61 |
| Standard deviation relative caspase activity (Run 3) | 0.05 | 0.05 | 0.04 |
| Average relative caspase activity (Run 4) | 1.37 | 1.33 | 2.15 |
| Standard deviation relative caspase activity (Run 4) | 0.09 | 0.26 | 0.30 |
| Average relative caspase activity (Runs 1, 2, 3, 4) | 1.29 | 1.31 | 1.58 |
| Standard deviation relative caspase activity (Runs 1, 2, 3, 4) | 0.11 | 0.04 | .047 |

The data of Table 1 illustrate that advantageous relative caspase activities, i.e. average relative caspase activity>1, were provided when cells were exposed to 15, 30, and 60 mM concentrations of trimethylpropane ethoxylate, as indicted by the respective average relative caspase activity (Runs 1, 2, 3, 4) values.

TABLE 2

|  | Trimethyl-propane ethoxylate [1.5 mM] | Trimethyl-propane ethoxylate [3 mM] | Trimethyl-propane ethoxylate [6 mM] |
|---|---|---|---|
| Average viability % (Run 1) | 130 | 74 | 65 |
| Standard deviation viability % (Run 1) | 36 | 32 | 17 |
| Average viability % (Run 2) | 133 | 114 | 72 |
| Standard deviation viability % (Run 2) | 16 | 23 | 8 |
| Average viability % (Run 3) | 114 | 120 | 59 |
| Standard deviation viability % (Run 3) | 15 | 19 | 7 |
| Average viability % (Run 4) | 72 | 72 | 31 |
| Standard deviation viability % (Run 4) | 34 | 55 | 9 |
| Average viability % (Runs 1, 2, 3, 4) | 112 | 95 | 57 |
| Standard deviation viability % (Runs 1, 2, 3, 4) | 28 | 26 | 18 |

The data of Table 2 illustrate that adequate viability, i.e. average viability % of 50% or greater for (Runs 1, 2, 3, 4), were provided after 24 hours when cells were exposed to 15, 30, and 60 mM concentrations of trimethylpropane ethoxylate.

TABLE 3

|  | 4-arm poly(ethylene glycol) [1.5 mM] | 4-arm poly(ethylene glycol) [3 mM] | 4-arm poly(ethylene glycol) [6 mM] |
|---|---|---|---|
| Average relative caspase activity (Run 1) | 1.30 | 1.39 | 1.27 |
| Standard deviation relative caspase activity (Run 1) | 0.10 | 0.12 | 0.10 |
| Average relative caspase activity (Run 2) | 0.97 | 0.89 | 1.17 |
| Standard deviation relative caspase activity (Run 2) | 0.07 | 0.32 | 0.13 |
| Average relative caspase activity (Runs 1, 2) | 1.14 | 1.14 | 1.22 |
| Standard deviation relative caspase activity (Runs 1, 2) | 0.23 | 0.35 | 0.07 |

The data of Table 3 illustrate that advantageous relative caspase activities, i.e. average relative caspase activity>1, were provided when cells were exposed to 1.5, 3, and 6 mM concentrations of 4-arm poly(ethylene glycol), as indicted by the respective average relative caspase activity (Runs 1, 2) values.

TABLE 4

|  | 4-arm poly(ethylene glycol) [1.5 mM] | 4-arm poly(ethylene glycol) [3 mM] | 4-arm poly(ethylene glycol) [6 mM] |
|---|---|---|---|
| Average viability % (Run 1) | 163 | 180 | 170 |
| Standard deviation viability % (Run 1) | 53 | 17 | 28 |
| Average viability % (Run 2) | 105 | 142 | 90 |
| Standard deviation viability % (Run 2) | 28 | 11 | 12 |
| Average viability % (Runs 1, 2) | 134 | 161 | 130 |
| Standard deviation viability % (Runs 1, 2) | 41 | 27 | 57 |

The data of Table 4 illustrate that adequate viability, i.e. average viability % of 50% or greater for average viability % (Runs 1, 2), were provided after 24 hours when cells were exposed to 1.5, 3, and 6 mM concentrations of 4-arm poly(ethylene glycol).

TABLE 5

|  | Glycerol ethoxylate [15 mM] | Glycerol ethoxylate [30 mM] |
|---|---|---|
| Average relative caspase activity (Run 1) | 1.13 | 1.03 |
| Standard deviation relative caspase activity (Run 1) | 0.11 | 0.20 |
| Average relative caspase activity (Run 2) | 1.13 | 1.14 |
| Standard deviation relative caspase activity (Run 2) | 0.19 | 0.08 |
| Average relative caspase activity (Run 3) | 1.20 | 1.12 |
| Standard deviation relative caspase activity (Run 3) | 0.07 | 0.11 |
| Average relative caspase activity (Run 4) | 1.23 | 1.13 |
| Standard deviation relative caspase activity (Run 4) | 0.08 | 0.17 |
| Average relative caspase activity (Runs 1, 2, 3, 4) | 1.17 | 1.11 |
| Standard deviation relative caspase activity (Runs 1, 2, 3, 4) | 0.05 | 0.05 |

The data of Table 5 illustrate that advantageous relative caspase activities, i.e. average relative caspase activity>1, were provided when cells were exposed to 15 and 30 mM concentrations of glycerol ethoxylate, as indicted by the respective average relative caspase activity (Runs 1, 2, 3, 4) values.

TABLE 6

|  | Glycerol ethoxylate [15 mM] | Glycerol ethoxylate [30 mM] |
| --- | --- | --- |
| Average viability % (Run 1) | 94 | 65 |
| Standard deviation viability % (Run 1) | 20 | 9 |
| Average viability % (Run 2) | 139 | 110 |
| Standard deviation viability % (Run 2) | 19 | 23 |
| Average viability % (Run 3) | 139 | 105 |
| Standard deviation viability % (Run 3) | 12 | 55 |
| Average viability % (Run 4) | 76 | 64 |
| Standard deviation viability % (Run 4) | 39 | 45 |
| Average viability % (Runs 1, 2, 3, 4) | 112 | 86 |
| Standard deviation viability % (Runs 1, 2, 3, 4) | 32 | 25 |

The data of Table 6 illustrate that adequate viability, i.e. average viability % of 50% or greater, for average viability % (Runs 1, 2, 3, 4) were provided after 24 hours when cells were exposed to 15 and 30 mM concentrations of glycerol ethoxylate.

What is claimed is:

1. A method of inducing caspase activity, the method comprising contacting a cell with a treatment compound formed by alkoxylation of an initiator using an oxide, wherein the treatment compound is one or more represented by the formula:

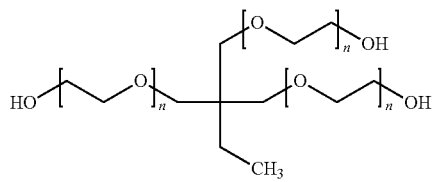

wherein each n is independently from 1 to 303;

the formula:

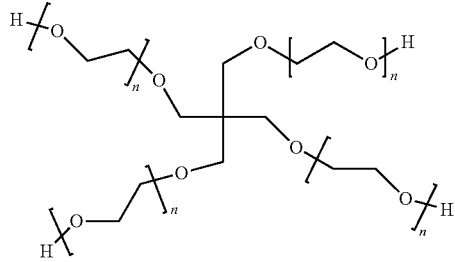

wherein each n is independently from 1 to 227; or the formula

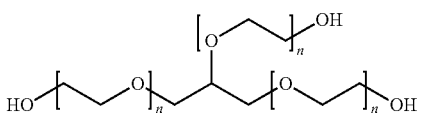

wherein each n is independently from 1 to 303.

2. The method of claim 1, wherein the initiator includes compounds containing three or more reactive available hydroxyl groups, amine groups, or combinations thereof.

3. The method of claim 1, wherein the initiator selected from glycerol, diglycerol, triglycerol, hexaglycerol, tripentaerythritol, trimethylolpropane, sorbitol, ethylenediamine, triethyleneamine, 2,2 bis (hydroxymethyl)-1,3-propanediol, ethanolamine, and combinations thereof.

4. The method of claim 1, wherein the oxide is selected from ethylene oxide, propylene oxide, butylene oxide, and combinations thereof.

5. The method of claim 1, wherein the treatment compound has a number average molecular weight from 400 to 40,000 g/mol.

6. The method of claim 1, wherein the treatment compound has a 0.001 millimolar to 75 millimolar concentration in a treatment medium.

7. The method of claim 1, wherein the cell is a cancerous cell.

8. The method of claim 1, wherein the caspase is an effector caspase.

9. The method of claim 1, wherein the caspase is selected from caspase 3, caspase 6, caspase 7, or combinations thereof.

10. The method of claim 1, further comprising inciting apoptosis.

11. The method of claim 1, wherein the treatment compound has a relative caspase activity greater than 1.

12. The method of claim 1, wherein the treatment compound has a relative caspase activity greater than 1.2.

13. The method of claim 1, wherein the treatment compound has a relative caspase activity greater than 1.5.

* * * * *